United States Patent
Frieze

(10) Patent No.: US 9,885,664 B2
(45) Date of Patent: Feb. 6, 2018

(54) DETECTION METHOD FOR ASSESSING THE EFFICIENCY OF A CLEANING OPERATION

(71) Applicant: Case Medical, Inc., South Hackensack, NJ (US)

(72) Inventor: Marcia A Frieze, Alpine, NJ (US)

(73) Assignee: Case Medical, Inc., South Hackensack, NJ (US)

( * ) Notice: Subject to any disclaimer, the term of this patent is extended or adjusted under 35 U.S.C. 154(b) by 0 days.

(21) Appl. No.: 15/144,864

(22) Filed: May 3, 2016

(65) Prior Publication Data

US 2016/0327490 A1 Nov. 10, 2016

Related U.S. Application Data

(60) Provisional application No. 62/156,423, filed on May 4, 2015.

(51) Int. Cl.

| | | |
|---|---|---|
| *G01N 21/78* | (2006.01) | |
| *B65D 43/16* | (2006.01) | |
| *A61B 90/70* | (2016.01) | |
| *C11D 3/386* | (2006.01) | |
| *B08B 11/02* | (2006.01) | |
| *B08B 13/00* | (2006.01) | |
| *G01N 21/88* | (2006.01) | |
| *G01N 21/94* | (2006.01) | |
| *B08B 3/12* | (2006.01) | |
| *G01N 21/76* | (2006.01) | |
| *G01N 21/91* | (2006.01) | |
| *G01N 21/77* | (2006.01) | |

(52) U.S. Cl.
CPC ............. *G01N 21/78* (2013.01); *A61B 90/70* (2016.02); *B08B 11/02* (2013.01); *B08B 13/00* (2013.01); *B65D 43/16* (2013.01); *C11D 3/386* (2013.01); *C11D 3/38627* (2013.01); *G01N 21/8803* (2013.01); *G01N 21/94* (2013.01); *A61B 2090/702* (2016.02); *B08B 3/12* (2013.01); *G01N 21/76* (2013.01); *G01N 21/91* (2013.01); *G01N 2021/7786* (2013.01)

(58) Field of Classification Search
CPC ...................................................... G01N 20/78
See application file for complete search history.

(56) References Cited

U.S. PATENT DOCUMENTS

| | | |
|---|---|---|
| 5,726,062 A | 3/1998 | Numa et al. |
| 6,107,097 A | 8/2000 | Pfeiffer |
| 6,315,124 B1 | 11/2001 | Hirohata et al. |
| 6,624,132 B1 * | 9/2003 | Man ................ C11D 3/046 510/321 |
| 2003/0032207 A1 | 2/2003 | Rengarajan et al. |
| 2004/0014298 A1 | 1/2004 | Ehrke et al. |
| 2005/0250089 A1 | 11/2005 | Chandrapati et al. |
| 2007/0249054 A1 | 10/2007 | Doi et al. |
| 2007/0267039 A1 | 11/2007 | Sullivan |
| 2007/0289614 A1 | 12/2007 | McDonnell et al. |
| 2008/0051310 A1 | 2/2008 | De Dominicis |
| 2011/0291830 A1 | 12/2011 | Kaiser |
| 2014/0314957 A1 | 10/2014 | Minami et al. |

FOREIGN PATENT DOCUMENTS

| | | |
|---|---|---|
| EP | 0151855 B1 | 5/1988 |
| WO | 1997027482 | 7/1997 |

OTHER PUBLICATIONS

Nayuni, et al; A new tool (Valipro (TM)) to optimse, validate and improve cleaning efficacy; Medical Device Decontamination May-Jul. 2014, vol. 18, No. 4, pp. 18-23.
PCT International Search Report and Written Opinion of the International Search Authority dated Sep. 1, 2016 in coresponding PCT application PCT/US2016/030526.

\* cited by examiner

*Primary Examiner* — Bin Shen
(74) *Attorney, Agent, or Firm* — Irving M. Fishman

(57) ABSTRACT

A method of assessing the efficiency of a cleaning operation and assessing likely residual contamination on substrates after a cleaning operation.

15 Claims, 2 Drawing Sheets

DETECTION METHOD FOR ASSESSING THE EFFICIENCY OF A CLEANING OPERATION

CROSS REFERENCE TO RELATED APPLICATIONS

This application claim priority of U.S. Provisional Application 62/156,423, filed May 4, 2015, the entirety of which is incorporated herein by reference.

FIELD OF THE INVENTION

The present invention is in the field of cleaning substrates that have potentially been contaminated with a variety of biological contaminants. In particular, the invention is in the field of cleaning of surgical instruments and utensils used in slaughtering operations in meat processing and the processes of carrying out such cleaning operations. The invention also relates to the field of utilizing surrogate detection systems for detecting improper cleaning and the detection system itself. The invention is further in the field of soak baths and automated cleaning processing of suitable substrates, and in particular (without limitation) to operations using ultrasonic and washer decontamination as well as verifying the effectiveness of single-enzymatic and/or multi-enzymatic detergents.

BACKGROUND OF THE INVENTION

Existing wash indicators on the market were and are designed primarily to monitor protein residuals or the effectiveness of alkaline cleaners. However, few if any of the currently and previously available wash indicators were able to monitor the effectiveness of pH neutral enzymatic cleaners and the presence of substrates that they were intended to remove. The prior indicators and systems were directed generally to protein, hemoglobin or fibrinogen. The prior wash indicators are simply not truly indicative of "clean" with respect to residues of other materials besides protein, hemoglobin or fibrinogen. However, multi-enzymatic cleaners are designed to remove or breakdown several organic soils in addition to protein, hemoglobin or fibrinogen.

The cleaning procedures in health care facilities have come under increasing scrutiny and the media has reported on various events where SSI (Surgical Site Infections) or HAIs (Hospital Acquired or Associated Infections) were acquired during routine procedures and some patients even died when various organic contaminants and bioburden were transmitted on contaminated surgical devices, even those visibly clean. For those devices that were seemingly clean (by visible inspection) it is clear that either small contamination levels not apparent to the naked eye AND/OR contaminants that are not visible because they have no visible light alteration properties so that they are "invisible" or "nonvisible" even if present in significant amounts are problematic and need to be addressed. These are not new problems, and have been around since the beginning of surgical techniques (if not earlier), but the concerns have been brought to the forefront of public awareness by the media.

The health care industry has used test soils that simulate organic soils to test the efficiency of cleaning systems. However, some are synthetic, a chemical or polymer that is washed away during reprocessing and supposedly designed to simulate true organic materials, but are not truly representative of the materials they are supposed to simulate. Some utilize hemoglobin and fibrin (a fibrous, non-globular protein involved in the clotting of blood, which is formed by the action of the protease thrombin on fibrinogen which causes the latter to polymerize. The polymerized fibrin together with platelets forms a hemostatic plug or clot over a wound site) on a substrate or coupon. However, the determination of results using these wash indicators rely on visual inspection only of an instrument or substrate to which the test soil is applied. This visual inspection provides a very limited way to determine if devices are safe for patient care.

Still, blood or fibrinogen may not be the most challenging of bodily materials to remove. Fat and brain tissue are particularly resistant to removal. When dried, these substances affix to stainless steel surfaces. Of particular concern is when inter-ocular tissue or neurological materials adhere to surgical devices. The user may not see any residual material with the naked eye, but believes that the device is safe to use on another patient. Blood with its distinctive color may be removed, but the "invisible" or "nonvisible" soil and bioburden can remain as residuals which are not recognized as being present.

The emergence of Creutzfeld Jackob Disease (CJD) transmissions from patient to patient via surgical procedures such as central nervous system, brain, eye, spleen, tonsils, appendix, as well as blood transfusions have pointed out the importance of routine monitoring of cleaning parameters beyond the visual check presently the norm in health care facilities. Moreover the presence of protein has been shown to increase corrosion of stainless steel instruments. In addition, the residual protein or lipids may promote adhesion of bacteria to device surfaces. The presence of protein and organic soil is also known to interfere with the sterilization process or further disinfection. Furthermore, staff may take short cuts, without recognizing the danger involved, when the requirement for inspection and release of devices is visual.

Each of the patents and patent applications mentioned in the next three paragraphs, are incorporated herein by reference in their entirety. To the extent that a statement in such reference is contrary to statements made herein (either made herein explicitly or implicitly) statements made herein shall prevail and the contrary or conflicting statement in the reference shall not be used to limit the scope of the invention. However, to the extent that any statement present in these references can provide support for a limitation to avoid prior art, either affirmatively or negatively, and applicant wishes to utilize such limitation in the claims, such shall be deemed incorporated, but only if and when Applicant requires such for introducing such a limitation into one or more claims.

US 20110291830 discloses a combination of a cleaning indicator, an associated test specimen, and a method for testing cleaning processes. This has a plurality of indicator elements on a common carrier to determine a differentiated determination of cleaning action.

WO97/27482 relates to sticking hemoglobin, a major component of blood, and albumin on a stainless steel plate with the use of fibrin. This, however, is not fully representative of bodily fluids or tissue. Blood is easily removed using an alkaline detergent, but alkaline detergents are corrosive to many devices used in surgical procedures. Further, tissue and fat are harder to remove than blood. Thus, the evaluation given by this disclosure is not completely suitable.

U.S. Pat. No. 5,726,062 discloses a method of detecting protein and a kit detecting protein using the same. A kit is disclosed, which includes a sampling means and a color forming reagent in combination. The step process disclosed is a multi-step process.

As discussed briefly above, there are additional challenges to medical device reprocessing due to the increasing complexity of surgical devices as well as emerging multiple drug resistant microorganisms and infectious agents that are difficult to remove from surfaces of devices and from lumens of minimally invasive devices present on surgical devices. These challenges, while previously present, have not been adequately addressed in the past other than in some instances to move to disposable equipment. As equipment becomes more complex and costly, the acceptability of "disposable devices" is simply not economically reasonable.

OBJECTS OF THE INVENTION

It is an object of one embodiment of the invention to provide a more completely representative surrogate for a contamination on a substrate which is to be processed in a cleaning operation to determine the recommendations for routine cleaning purposes with a given cleaning system.

It is another object of an embodiment of the invention to provide a substrate soiled with a surrogate for a typical contamination which is to be processed in a cleaning operation in parallel with a substrate needing to be cleaned.

It is yet another object of an embodiment of the invention to provide a process of cleaning (in parallel fashion) both a soiled substrate needing to be cleaned and a surrogate therefor having a surrogate contamination thereon and exposing the surrogate to a contamination disclosing material in order to assess, in whole or in part, the effectiveness of the cleaning operation, without applying the disclosing material to the actual substrate needing cleaning.

Still a further object of the invention is to provide a device for carrying out the simultaneous, parallel cleaning operation of a substrate needing to be cleaned and a surrogate therefor.

Still another embodiment of the invention is to provide a method to verify the effectiveness of the washing equipment and parameters used prior to daily operations.

Yet other objective of the invention will be apparent to those of ordinary skill in the art upon having read the instant specification.

BRIEF DESCRIPTION OF THE INVENTION

The present invention is, in part, a detection method that can be used to better qualify whether a particular cleaning method or particular cleaning equipment or particular manner of using such cleaning equipment is truly functioning in a manner such that the end result is a cleaned substrate. The invention is also, in part, a detection method that involves a non-infectious surrogate (for potentially potential contaminants) on a surrogate substrate where the non-infectious surrogate is representative of a wide range of potential contaminates, the non-infectious surrogate contaminates being on a surrogate (for the actual substrate in need of cleaning) substrate, and the surrogate substrate with the surrogate contaminates being subjected simultaneously to the same cleaning process as the actual substrate in need of cleaning, with the surrogate substrate being exposed to contaminate disclosing components to determine whether the non-infectious surrogate contaminant has been adequately removed from the surrogate substrate. The invention is also, in part, a device for cleaning the aforementioned substrates in the same manner at the same time in a single bath.

DETAILED DESCRIPTION OF THE SEVERAL EMBODIMENTS OF THE INVENTION

Figure 1:
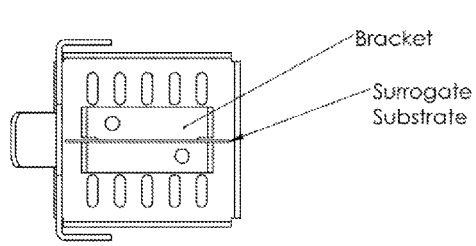
FIG. 1 is a top view of one embodiment of a surrogate substrate container useful in the present invention in an open position.

The present invention is directed in part to a surrogate cleaning method and the components used therein and to kits for use in such methods. One aspect of the invention is the scope of the "surrogate" contaminate. In order to be a trusted surrogate, it must emulate as many parameters as possible that are relevant of the real world potential contaminants. Current non-infectious "surrogate" contaminants fall woefully inadequate for the purpose when one considers the medical issues being highlighted in the media in recent years, notwithstanding that these issues have been present for much longer periods of time. For purposes of the present invention, the non-infectious "surrogate" contaminant is a blend comprising calf serum, rabbit blood, milk solids, gelatin, carbohydrates, starches, and other components simulating various bodily materials and fluids. Those of ordinary skill in the art will recognize alternative sources of blood, serum, mammalian milk solids, gelatin, carbohydrates, starches, etc. for use in creating the "non-infectious surrogate contaminant". The particular surrogates chosen for use in any particular non-infectious surrogate contaminant composition can be generalized or may be configured to match up with particular enzymes that are being used in a particular cleaning formulation, as discussed more fully below. Relative concentrations of the various components of the non-infectious surrogate contaminant are not critical, rather their presence as a portion of the surrogate for the contaminant is important. In some embodiments, non-infectious bacteria or other non-infectious microorganisms may also be included in the non-infectious surrogate contaminant. While the various surrogate contaminant components may be applied to a surrogate substrate independently, a preferred manner of applying the non-infectious surrogate contaminant components is to create a single blend of the various components and apply it to the surrogate substrate as a single blend. This helps in that the various subcomponents are throughout the applied surrogate contaminant layer on the substrate and there is no one component that may be hidden form action of the cleaning agents due to the construction of the non-infectious contamination layers on the surrogate substrate.

Where desired, a particular non-infectious surrogate contaminant may be matched to entities that are cleaned by or attacked by or destroyed by enzymes in a particular enzymatic cleaner (which may contain one or more enzymes, and preferably has two or more enzymes) or multi-enzymatic cleaner that is being used in a particular cleaning regimen. In such cases, those of ordinary skill will know which types of components to include in the non-infectious surrogate contaminant composition based on the enzymatic composition. For example, an enzymatic composition having a protease and a lipase only would have at least proteins and lipids in the non-infections surrogate contaminant that are susceptible to attack or cleaning by those enzymes. Notwithstanding this, the non-infectious surrogate contaminant could have additional substances that these enzymes would not be effective against, but that would not detract from the scope and tenor of the present invention. Having fewer materials in the non-infectious surrogate contaminant than at least one member that is susceptible to the attack and/or cleaning action of each enzyme (i.e., one or more enzymes in the respective cleaner would not have a non-infectious contaminant member that it would work on) would render the invention less advantageous as it would not be expected to be a suitable surrogate for the enzyme for which cleaning activity is not being assessed by the method. However, such embodiments remain within the invention, provided at least a protein is present in the surrogate contaminant composition, additional components for the surrogate contaminant composition may include, without limitation, blood, serum, a fat or lipid, a carbohydrate, some type of tissue (preferably brain or ocular tissue or other nervous system tissue), mucous, and albumin. The more components in the surrogate contaminant composition, the better able the surrogate contaminant composition can truly represent the actual contaminants which may be present on an actual substrate being cleaned in the present process. Nonetheless, those of ordinary skill in the art will be able to selectively choose which of such surrogate contaminant components are desired in the surrogate contaminant composition.

The surrogate substrate can be of any suitable material and any suitable construction. Preferably, the material of the substrate is selected from materials used in surgical and other medical applications, most preferably stainless steel (as used in most surgical instruments). The construction of the surrogate substrate may be of any desired shape. While simple "coupons" are most convenient, in order to simulate cleaning issues that may arise from lumens or various connection points, it is preferable to have one or more screws or bolts through the coupon in a reasonably tightened position as well as one or more lumens mounted on the surrogate substrate. The lumens may be of stainless steel, but preferably are clear tubes or composite lumens made up of a stainless steel portion and a visibly clear portion (generally plastic) so that if one were to remove the visibly clear portion, the two halves would resemble a straw cut longitudinally into two pieces. When present the lumens should be of an internal diameter of approximately the same sizes that are found in the actual substrates being processed for cleaning, but there is no requirement to match up the lumen internal diameter size. The advantage to matching up the internal lumen size as closely as possible is that the closer the lumen internal diameter matches the actual size of the lumens in the actual substrate, the more predictive of suitable or unsuitable cleaning is the present invention method. By providing the screws and lumens recesses where contaminants may have partial protection from the cleaning solution or cleaning operation and therefore may be more problematic in being removed during such operations than would be evident from a smooth surfaced coupon being processed under similar circumstances are present and a more accurate assessment of proper cleaning can be made with the present invention. A test soil indicator representative of various organic contaminants found on surgical devices for example those evident from surgical procedures, such as endoscopy, spine or orthopedic procedures addresses a wider range to possible residues and provides more accurate information as to whether a device is safe to release.

After processing the surrogate substrate having the surrogate contaminants thereon in the cleaning operation, one or more disclosing compositions (preferably solutions) are applied to the surrogate substrate that has been supposedly cleaned to see if in fact the surrogate substrate has been truly cleaned. In the situations in which the cleaning operation is being conducted to determine the proper parameters to use in cleaning actual substrates needing to be cleaned, detection of still residual contaminants indicates that the cleaning parameters need to be adjusted and those of ordinary skill will be able to suitably adjust such parameters, which may include, without limitation, adjustments to cleaning agent formulations (such as without limitation, concentrations, pH, enzymatic and surfactant components, etc.), contact time, temperature, use or non-use of ultrasonics and/or shaking of the bath, and the incorporation or omission of a hand scrubbing step. If a suitable cleaning result is obtained, one may accept the used parameters or further adjust the parameters to less costly ones, re-run the cleaning operation with additional surrogate substrate having surrogate contaminants thereon and evaluate the results thereof, repeating the process until such time as an unsuitable result is obtained. This allows for one to standardize the cleaning operation to one that is both effective and most economic, but preferably not at the limit of acceptability so as to give a safety margin. Those of ordinary skill in the art will be able to select these parameters once having the benefit of the present invention. The invention cleaning operation can be used on a regular schedule, prior to, subsequent to, or simultaneously with use of the cleaning equipment to clean a substrate in need of cleaning in order to verify/validate that the cleaning operation is working correctly. Preferably, such a verification run is performed on a daily basis.

A disclosing composition (preferably a protein disclosing solution, most preferably a disclosing solution having disclosing components for multiple components of the surrogate contaminant composition) is used following the cleaning operation, and simply applied as a second step increases the effectiveness of the inspection process. Once a cleaning operation protocol has been determined, actual substrates needing to be cleaned and surrogate substrates having the surrogate contaminants on the surrogate substrate are placed in suitable containers and subjected to the same cleaning operation in a single bath. At the conclusion of the cleaning operation, a suitable disclosing formulation is applied to the supposedly cleaned surrogate substrate to determine if any of the surrogate contaminants remain thereon. If surrogate contaminants are found thereon, the supposedly cleaned actual substrate is deemed not sufficiently cleaned and (a) reprocessed in the same or more aggressive cleaning operation, or (b) sent to available laboratory facilities for a detailed determination of the contaminants remaining. If the disclosing composition does not reveal any residual surrogate contaminant on the surrogate substrate, the actual supposedly cleaned substrate is deemed cleaned sufficiently to be released and forwarded on to the next step of the cleaning and/or disinfection and/or sterilization procedure (as appropriate).

Disclosing compositions for use in the present invention include, without limitation, disclosers for any of the components of the surrogate contaminant composition, and preferably have at least one disclosing agent that is sensitive for any one or more surrogate contaminant component, with preferably each surrogate contaminant component having at least one discloser in the disclosing composition. At a minimum, a protein discloser component is present in at least one of the disclosing compositions used. Use of sequentially applied disclosing compositions having fewer disclosing agents than those needed to detect all of the components of the surrogate contaminant components can be used, but is less preferable as being inherently less reliable than a single disclosing composition. Nonetheless, when the disclosing components must be in separate compositions due to chemical incompatibilities or disclosing formulation instability issues, use of such sequential disclosing formulations is necessary. When separate, sequential detection compositions are used, a protein disclosing composition is preferably used first as residual proteins is generally the more problematic of residual contamination after cleaning.

Utilizing the various disclosing compositions allows for visible detection of otherwise "invisible" or "nonvisible" surrogate contaminant components resulting from the cleaning step just completed, and thus gives assurance that the substrate being cleaned is clean. Disclosing compositions for use in the present invention are generally known materials and include, those for proteins (such as without limitation Bradford's reagent, Coomashie Blue, and/or Coomashie Orange or Ninhydrin (ninhydrin detects ammonia or primary and secondary amines by producing deep blue or purple color known as Ruhemann's purple on reaction with such amines), or use of chemical or bioluminescence or chemical or bio-fluorescence; those for starches such as iodine, those for lipids, etc. which may be known in the art. Where a simple disclosing composition is not readily available for a suspected component, the surrogate substrate with the residual material thereon (or the residual material by itself) can be forwarded to laboratory facilities for independent confirmation of the residual matter.

In practice, a surrogate substrate, generally stainless steel, which may be a simple coupon, or a coupon having representative surface imperfections such as screws, crevices, surface scratches, occluded areas and or lumens representative of those used in the actual substrates to be cleaned, is coated with a cocktail of representative test soils representative of various organic materials found on surgical devices after surgery. The test soils will be made of sterile materials which will be dried onto the coupon at preferably designated locations, but may cover the entire surface and be introduced into surface imperfections and lumens that are present. A clearly defined area on the coupon may be marked in any desired pattern, such as without limitation, circular, square, rectangular, or "X", such that a solution of disclosing agent can be applied to determine if any residual, "invisible" or "nonvisible" soil or protein is present after processing. However, the disclosing solution may be applied (subsequent to the alleged cleaning step) to the entire surface of the allegedly cleaned surrogate substrate coupon if so desired.

The coupon having the surrogate contaminants thereon is placed in a small perforated case or holder in the center of a perforated box secured by a bracket which will hold the coupon in place during the automated cleaning process. Where the cleaning operation is a simple soak, with or without sonication or with or without shaking, the box may or may not be used, and if not used, the surrogate substrate with the surrogate contaminants thereon may simply be placed in the same case or holder (or a parallel case or holder) or basin as the items being cleaned to determine the effectiveness of the cleaning solution for soaking without agitation, mechanical action or sonication. The case/holder and box are perforated to a degree, by providing some occlusion as one would find when multiple devices are placed within a tray with other items or within a perforated box during mechanical cleaning while allowing for free flow of cleaning solutions used in the cleaning step to wash and contact the surrogate contaminants in the identical manner as an actual substrate to be cleaned so that the cleaning operation on the surrogate substrate is in fact a suitable proxy for the cleaning action on an actual substrate being cleaned. In operations where cleaning equipment parameters are being defined, the surrogate substrate (coupons) having the surrogate contaminant composition thereon may be used alone or placed within the case holder to withstand the mechanical cleaning action. In operations where an actual cleaning is taking place, the actual substrate needing cleaning is placed in the cleaning solution in an appropriate container for normal cleaning operations and the surrogate coupon having the surrogate contaminants thereon may be placed in a small perforated case or holder in a box having an attachment portion for attaching the box to the washer rack or other container (the other container used to hold the actual substrate being cleaned). The box/holder/case are each perforated with holes that permit flow of fluid so that the surrogate substrate and the actual substrate are simultaneously exposed to the same cleaning operations in the same equipment in the same solutions. A lid may be further used to secure the device in place, but need not be used. A hook on the exterior of the case allows the user to attach the case to the washer rack or to be held vertically along the basket or insert side wall. Simply put, the small case with coupon installed within can be placed within the wash basket for a simulated test of machine/equipment, wash/cleaning process, and detergent efficiency.

Once the wash/cleaning operation is completed, the disclosing solution is applied to the surrogate substrate by any suitable means that does not disrupt any contaminants that remain on the surface. Typically, the disclosing solution is applied by, without limitation, an eye dropper, sprayer or droplet application. The disclosing solution can be applied manually or can be automated, but is preferably manually applied as the surrogate substrate can be separated from the actual substrate being cleaned so that disclosing solution can be more assuredly not applied to the actual substrate being cleaned when applying disclosing solution to the surrogate substrate. Alternatively, the disclosing solution can be applied utilizing a syringe or dispensing device or a robotically controlled or programmed dispenser such that a consistent amount of disclosing solution is applied for a more accurate determination of contaminant reduction, such as, without limitation when sending the result to a lab to determine the reduction. A circular spot or other locator is generally present as a guide for visible detection of retained soil as well as for application of the protein detector solution. This spot can be scratched, punched, lasered or embossed onto the surface of the surrogate substrate to serve as a locator to apply the protein detecting solution onto the visibly "clear or cleaned" surface. However, where the surrogate contaminants are applied across a significant portion of the entire surface of the coupon (or all of it), the indicia (visible markings of areas) of where to apply the disclosing solution is less important, and in such cases, may be omitted.

While other wash monitors are designed specifically for automated washers only or for specific detergents, the present invention allows for a standardized surrogate substrate with the cocktail of surrogate contaminant test soils to be used to determine the effectiveness of any of soaking (with or without agitation, with or without an ultrasonic energy applied), by simply placing the surrogate substrate with the surrogate contaminants thereon in a solution of the representative cleaning products in a representative soak receptacle, as well as in an automated process.

Figure 4:
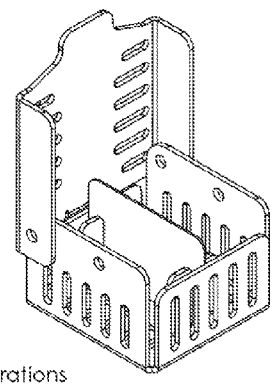
FIG. 4 is a perspective view of the container of FIG. 1.
Figure 2:
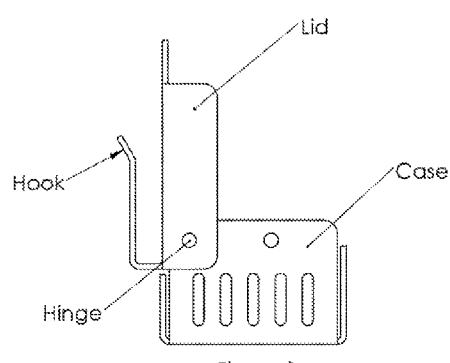
FIG. 2 is a left side view of the container of FIG. 1.
Figure 3:
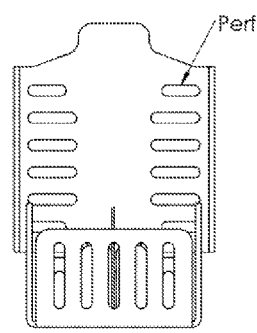
FIG. 3 is front view of the container of FIG. 1.
Figure 5:
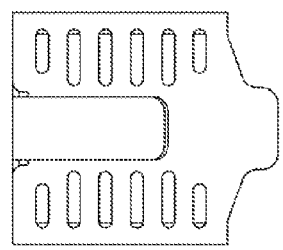
FIG. 5 is a top view of the container of FIG. 1 in a closed position.
Figure 6:
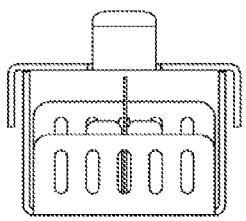
FIG. 6 is a front view of the container of FIG. 5.
Figure 7:
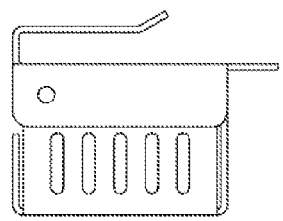
FIG. 7 is a left side view of the container of FIG. 5.
Figure 8:
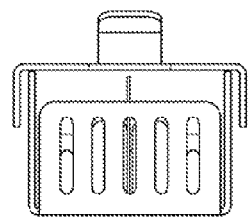
FIG. 8 is a right side view of the container of FIG. 5.
Figure 9:
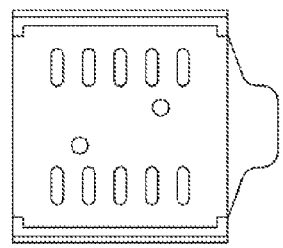
FIG. 9 is a bottom view of the container of FIG. 5.

With reference to the Figures, FIGS. 1-4 show a container (in an open position) for containing the surrogate substrate for use in the present invention FIGS. 5-9 show the same container in a closed position. While shown in a rectangular shape, the particular shape is not of any consequence, although square or rectangular shapes are convenient for space saving purposes. The lid, shown in FIGS. 1-4 in an open position is hinged to side walls through any suitable hinging mechanism such as rivets, screws, hinges, etc. The lid has a hook for hanging the container on a wash rack or on a basket either of which wash rack or basket may contain an actual substrate that is being cleaned in a simultaneous operation with the surrogate substrate. Perforations in the top, bottom, and side walls are shown in one particular shape, but the shape is not of consequence and these perforations may be of any suitable shape and size that does not impede the free flow of cleaning solution in the particular cleaning operation. In FIGS. 1, 3, 4, 6, and 8, can be seen the surrogate substrate after it has been placed in the container, and held in place by the bracket.

Having described the invention above, the following non-limiting examples are provided to exemplify, but not limit, the invention, which is only limited by the claims as appended hereto or finally amended as ultimately issued.

EXAMPLES

Example 1

A surrogate substrate which is a stainless steel coupon has a surrogate contamination solution having a "Red" Food coloring added thereto applied to a defined area. The coupon is used as a surrogate in a cleaning operation for determination of the efficiency of the cleaning operation or as a surrogate for determination of whether to conclude a cleaning operation has cleaned a particular product.

Example 2

In a perforated case having a lid, the case further having an inner bracket for engaging a surrogate substrate, such as, without limitation, the surrogate substrate of Example 1, and a hook for engaging with a washer rack or a wall of a basket so as to affix the perforated case to the washer rack or the wall of the basket, the surrogate substrate with the surrogate contaminants thereon is placed. The perforated case is attached to either the washer rack of a washer or a basket and subjected to a cleaning operation.

Example 3

On completion of the cleaning operation in Example 2, the coupon is examined for any remaining "red" portions, which are indicative of not having cleaned off the surrogate contaminants. None having been found, the apparently clean surrogate substrate is sprayed with Bradford's reagent in order to reveal any previously "invisible" or "nonvisible" protein remnants. On spraying the coupon, no color change is seen, indicating that the surrogate substrate has passed and therefore the actual substrate being cleaned simultaneously therewith is deemed clean and can pass on to the next step in the cleaning/disinfection/sterilization process.

Example 4

Example 3 is repeated except that on application of the Bradford's reagent, a color change is noted, indicating that insufficient cleaning has taken place. The actual substrate being cleaned is pulled from the cleaning process and forwarded to a lab for more definitive determination of the residual material.

Example 5

Example 4 is repeated except that instead of sending the actual substrate being cleaned to a lab for more detailed determinations of contamination, the substrate is then cleaned using a more rigorous cleaning step.

Example 6

A kit is prepared for sale containing at least
  the surrogate substrate with surrogate contaminants thereon
  a protein disclosing agent solution
  optionally, a surrogate substrate holder for holding the surrogate substrate and attaching to either a wash rack or a basket Example 7

Example 3 is repeated except that instead of simultaneously running the actual substrate needing cleaning with the surrogate substrate having the surrogate contaminant solution thereon, the cleaning equipment is first validated by running the cleaning equipment using the surrogate substrate with the surrogate contaminant composition thereon and if the surrogate substrate is adequately cleaned, then running the cleaning operation with an actual substrate in need of being cleaned.

Example 8

Example 3 is repeated except that instead of simultaneously running the actual substrate needing cleaning with the surrogate substrate having the surrogate contaminant solution thereon, the cleaning equipment is first run in an actual cleaning operation to clean an actual substrate in need of being cleaned and then subsequently, the same equipment is run in the same cleaning operation using a surrogate substrate having a surrogate contaminant composition thereon in order to validate the effectiveness of the cleaning operation with the equipment in question.

I claim:

1. A method of assessing whether a cleaning operation has cleaned an actual substrate, said method avoiding exposure of said actual substrate to a disclosing solution, said method comprising:
  utilizing a surrogate substrate having a clearly defined area thereon which clearly defined area survives said cleaning operation, having a surrogate contaminant thereon at least within the clearly defined area,
  wherein said surrogate substrate comprises a material comparable to said actual substrate and said surrogate contaminant is non-infectious and comprises at least one material representative of a wide-range of potential actual contaminants of actual substrates in use, said surrogate contaminant components selected from the group consisting of blood, serum, fats, lipids, carbohydrates, starches, proteins, mucous, components that otherwise simulate body materials or body fluids, and mixtures thereof and said surrogate contaminant mimics in composition a generally known contaminant or contaminant combination that is generally contaminating said actual substrate post use and prior to being cleaned, said actual substrate potentially having infectious components thereon, while said surrogate contaminants having non-infectious corresponding materials that are similar to said infectious materials that are desired to be cleaned off of said actual substrate in need of being cleaned;

said method further comprising either simultaneously or sequentially in any order:

a) placing said surrogate substrate in a perforated partially occlusive surrogate holding container, said surrogate substrate having said surrogate contaminant formulation thereon, and placing said container into an area where said surrogate substrate with said surrogate contaminant formulation thereon is exposed to a first cleaning operation, b) placing an actual substrate, having a contaminant composition thereon in need of cleaning in a main substrate cleaning compartment, whereby said actual substrate with said contaminant thereon is exposed to a second cleaning operation;

said first and said second cleaning operations being identical and conducted in the same unit of cleaning equipment using the same cleaning composition formulation any order or simultaneously, said cleaning compositions comprising at least one component selected from proteases, lipases, enzymes that act on carbohydrates, enzymes that act on starches, surfactants, and mixtures thereof and optionally other known cleaning composition components;

wherein said perforated surrogate holding container is either (I) removably attached to said main substrate cleaning compartment, (II) forms a distinct area within said cleaning equipment from said main substrate cleaning compartment, or (III) when said first and said second cleaning operations are sequential to one another may further be the same as said main substrate cleaning compartment, so that both said substrate in need of cleaning and said surrogate substrate may be subjected to the identical cleaning operation either simultaneously or sequentially;

c) visually inspecting at least the supposedly clean surrogate substrate for cleaning; and d) if said supposedly clean surrogate substrate appears clean, then e) below or d)(i) below (i) validating said cleaning process on a regular schedule by treating said supposedly clean surrogate substrate with at least one disclosing solution to at least said clearly defined area, which disclosing solution produces a detection signal for at least one non-visible or invisible component of said surrogate contaminant formulation indicative of residual contamination when said residual contamination is present; inspecting the same for said signal indicative of residual contamination; and (ii) if said inspection of step (d)(i) shows no signal indicative of residual contamination, then (e) below, and if said step (d)(i) shows a signal indicative of residual contamination then (f) below:

(e) deciding that said actual substrate needing to be cleaned is clean when put through the same cleaning operation with the same cleaning composition formulation and the same cleaning operation parameters as was used for the surrogate substrate having the surrogate contaminant thereon whereby said disclosing solution is not applied to said actual substrate in the course of concluding that the actual substrate is clean; and (f) if said visual inspection in step (c) above or said inspection in step (d)(i) yields an indication that said surrogate substrate still retains contaminants thereon or said actual substrate upon visual inspection shows remaining residual contaminants, concluding that said actual substrate is not adequately cleaned.

2. The method of claim 1 wherein said cleaning operation is validated on a regular schedule prior to, subsequent to, or simultaneous with use of the cleaning equipment to clean a substrate in need of cleaning.

3. The method of claim 1 wherein said cleaning operation is validated on at least a daily basis.

4. The method of claim 1 wherein said cleaning operation includes a sonic bath.

5. The method of claim 1, wherein said container comprises a bottom, a top, and at least one side wall combining to define an interior, at least one said top, said bottom, and said at least one side wall having perforations so as to allow for the free flow of cleaning composition into said interior, the container further having in the interior a holding portion for holding in said interior a substrate for a cleaning operation to be performed thereon, said top being removable mounted or hingably mounted on said side wall so that access into said interior to place a substrate for cleaning therein is permitted, and optionally an attachment member on a portion of said container for removably attaching said container to a basket or washer rack.

6. The method of claim 5 wherein said container at least one side wall is four walls in a rectangular orientation to one another, each of said top, said bottom, and said four side walls is perforated and said attachment member is a hook, and said top is hingably mounted.

7. The method of claim 1 wherein said surrogate substrate has a surrogate contamination composition thereon, wherein said surrogate contamination composition comprises at least a protein.

8. The method of claim 1 wherein said surrogate contaminant composition comprises at least a brain tissue.

9. The method of claim 1 wherein said cleaning composition has a single enzyme.

10. The method of claim 1 wherein said cleaning composition has at least 2 enzymes.

11. The method of claim 1 wherein said cleaning operation includes a soak bath, with agitation or without agitation.

12. The method of claim 1 wherein said at least one disclosing solution includes a disclosing solution that generates a signal via a chemical or bio-luminescence or chemical or bio-fluorescence mechanism.

13. The method of claim 1 wherein said first and second cleaning operations are automated cleaning operations.

14. The method of claim 1 wherein said surrogate substrate is stainless steel.

15. A method of determining appropriate procedures for cleaning substrates comprising (a) placing said at least one surrogate substrate having a clearly defined area thereon which clearly defined area can survive being subjected to a cleaning operation, in a perforated partially occlusive surrogate holding container, and (b) placing said container into an area where said surrogate substrate with said surrogate contaminant formulation thereon can be exposed to a cleaning operation to obtain a supposedly clean surrogate substrate, (c) exposing said surrogate having said surrogate contaminant formulation on at least said clearly defined area, to said cleaning operation;

(d) visually inspecting the supposedly clean surrogate substrate for residual contaminants; and (e) if said supposedly clean surrogate substrate appears clean, then (g) below or further validating said cleaning operation on a regular schedule by treating said supposedly clean surrogate substrate on said regular schedule with at least one disclosing solution, which disclosing solution produces a detection signal for at least one non-visible or invisible component of said surrogate contaminant formulation indicative of residual contamination when said residual contamination is present; and inspecting the same for said signal indicative of residual contamination;

(f) if said step (d) or (e) shows an indication
of residual contamination, modifying at least one of said cleaning operation parameters and repeat steps a-f using the modified parameters and if said signal is missing conclude that said conditions are then appropriate; and (g) concluding that an actual substrate having an actual contaminant thereon has or will be adequately cleaned when subjected to said cleaning operation in the same unit of equipment under identical cleaning operation parameters using identical cleaning composition formulation that has been used to clean said surrogate contaminants from said surrogate substrate.

* * * * *